US009741228B1

(12) United States Patent
Reich et al.

(10) Patent No.: US 9,741,228 B1
(45) Date of Patent: *Aug. 22, 2017

(54) PERSONAL SAFETY TRACKING USING AN APPARATUS COMPRISING MULTIPLE SENSORS

(71) Applicant: iSHADOW Technology Inc., San Diego, CA (US)

(72) Inventors: Stuart Reich, San Diego, CA (US); Dee Narla, Glendale, AZ (US)

(73) Assignee: iSHADOW Technology Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/987,550

(22) Filed: Jan. 4, 2016

Related U.S. Application Data

(63) Continuation of application No. 14/743,872, filed on Jun. 18, 2015, now Pat. No. 9,251,686, which is a continuation of application No. 14/727,695, filed on Jun. 1, 2015, now abandoned.

(51) Int. Cl.
   *G08B 23/00* (2006.01)
   *G08B 21/08* (2006.01)

(52) U.S. Cl.
   CPC .................................. *G08B 21/088* (2013.01)

(58) Field of Classification Search
   CPC .... G08B 21/02; G08B 21/0202; G08B 21/04; G08B 21/0453; G08B 21/08; G08B 21/088; G08B 21/22; H04H 20/59
   USPC ...... 340/984, 573.6, 573.1; 455/404.1, 404.2
   See application file for complete search history.

(56) References Cited

U.S. PATENT DOCUMENTS

| 6,157,303 | A  | 12/2000 | Bodie et al.   |
|-----------|----|---------|----------------|
| 8,038,213 | B2 | 10/2011 | Owens          |
| 8,149,124 | B2 | 4/2012  | Hoffman et al. |
| 8,730,049 | B2 | 5/2014  | Cutler et al.  |
| 8,768,292 | B2 | 7/2014  | Welch          |

(Continued)

OTHER PUBLICATIONS

International Search Report and Written Opinion of the International Searching Authority, for International Application No. PCT/US16/35319, dated Aug. 18, 2016, 9 pages, issued by the United States International Searching Authority.

*Primary Examiner* — Thomas Mullen
(74) *Attorney, Agent, or Firm* — San Diego Intellectual Property Law

(57) ABSTRACT

A system and method for facilitating personal safety tracking monitoring via an apparatus with multiple sensors are disclosed. The sensors may include a water sensor, an accelerometer, a water pressure sensor, an ambient temperature sensor, and/or any other sensors. The apparatus may be configured to generate various alerts in response to signals generated by the sensors. For example, the apparatus may generate a drowning alert when a submersion signal is generated and a drowning acceleration signature is detected in the same period. As another example, an abduction alert may be generated when an abduction acceleration signature and an out-of-boundary situation is detected for the apparatus. The alerts generated by the apparatus may be transmitted to a server or a client device associated with the apparatus for further processing, which may include generating a notification for presentation on the client device in response to an alert being received from the apparatus.

8 Claims, 10 Drawing Sheets

(56) References Cited

U.S. PATENT DOCUMENTS

| | | |
|---|---|---|
| 2006/0012483 A1 | 1/2006 | Ethington |
| 2007/0106172 A1* | 5/2007 | Abreu ................. A61B 5/0002 600/549 |
| 2007/0123121 A1 | 5/2007 | Quintero |
| 2007/0247307 A1 | 10/2007 | Riep |
| 2009/0289844 A1 | 11/2009 | Palsgrove et al. |
| 2009/0295566 A1 | 12/2009 | Weintraub |
| 2009/0309739 A1 | 12/2009 | Ezer et al. |
| 2010/0267361 A1 | 10/2010 | Sullivan |
| 2011/0187538 A1 | 8/2011 | Hawkins |
| 2011/0234397 A1 | 9/2011 | Fetzer et al. |
| 2012/0050101 A1 | 3/2012 | Whiteman |
| 2013/0217332 A1 | 8/2013 | Altman et al. |
| 2014/0049394 A1 | 2/2014 | Snyder et al. |
| 2014/0118149 A1 | 5/2014 | Elias |
| 2014/0306838 A1 | 10/2014 | Beumler |
| 2014/0323079 A1 | 10/2014 | Paolini |
| 2015/0116116 A1 | 4/2015 | Yang |
| 2015/0194031 A1 | 7/2015 | Cutler et al. |

* cited by examiner

PERSONAL SAFETY TRACKING USING AN APPARATUS COMPRISING MULTIPLE SENSORS

CROSS REFERENCE TO RELATED APPLICATIONS

This application is a continuation of U.S. patent application Ser. No. 14/743,872, filed on Jun. 18, 2015, now U.S. Pat. No. 9,251,686, which is a continuation of U.S. patent application Ser. No. 14/727,695, filed on Jun. 1, 2015, now abandoned, both of which are incorporated herein by reference.

FIELD OF THE INVENTION

The invention generally relates to facilitating personal safety tracking.

BACKGROUND OF THE INVENTION

We live in a world full of hazards that may endanger our children unexpectedly. For example, over-temperature is a hazardous condition when the ambient temperature increases significantly to cause hyperthermia to a child. Likewise, under-temperature is a hazardous condition when the ambient temperature decreases significantly to cause hypothermia to a child. By way of example, over-temperature may occur in a heated kitchen area, near a fireplace or a campfire, in a parked car or a room with a damaged air heater; and under-temperature may occur in a situation such as in a locked car in cold weather or in a room with a damaged air conditioner. Another example of a hazard would involve natural or man-made bodies of water like lakes, ponds, puddles, beaches, rivers, waterfalls or man-made water hazards like a swimming pool, Jacuzzi, hot tub, and/or fountain. Children, especially younger ones, are susceptible to drowning due in part to their inability to perceive potential dangers associated with those bodies of water. We also live in a world where children are abducted. Avoiding the above mentioned hazards and threats is not an easy task for any parent.

SUMMARY OF THE INVENTION

In accordance with one aspect of the invention, a system and method for facilitating personal tracking via an apparatus are disclosed. The apparatus may comprise multiple sensors that can detect events or changes in an environment the apparatus is exposed to. In some examples, the apparatus comprises a water sensor configured to detect that the apparatus is submerged into a body of water and to generate a submersion signal when such an event is detected; an accelerometer configured to measure acceleration of the apparatus and to generate an acceleration signal reflecting the acceleration of the apparatus; and/or any other sensors. In those examples, the apparatus may be configured to detect whether a drowning situation has occurred based on the submersion and acceleration signals; and if the apparatus detects that the drowning situation has occurred, the apparatus may generate a drowning alert for presentation on a client device associated with the apparatus. In one embodiment, without limitation, the apparatus is a wearable device and the client device is a mobile device such as a smartphone. In that embodiment, the drowning alert generated by the apparatus is transmitted over a communications network to the client device.

In some examples, the apparatus is configured to detect at least one of an abduction acceleration signature and a neutral acceleration signature based on the acceleration signals generated by the accelerometer. The neutral acceleration signature detected by the apparatus may reflect a pattern of acceleration by the apparatus, such as walking, running, biking, or riding in a vehicle. The abduction acceleration signature generated by the apparatus may reflect a pattern of abnormal acceleration by the apparatus within a time period that indicates the user carrying the apparatus may be subject to an abduction situation.

In some examples, the apparatus comprises a geo-location receiver configured to receive geo-location signals and to determine location coordinates of the apparatus. In those examples, the apparatus may be configured to receive location boundary information for boundaries of one or more areas, for example, from the client device or from a server; and to determine whether the apparatus is outside a boundary of the one or more areas by comparing the location coordinates and location parameters indicated by the location boundary information. In one embodiment, without limitation, the apparatus is configured to generate a wandering alert when it determines that the apparatus is outside the boundary of the one or more areas and detects the neutral acceleration signature in the same time period. In one embodiment, the apparatus is configured to generate an abduction alert when it determines that the apparatus is outside the boundary of the one or more areas and detects the abduction acceleration signature in the same time period.

In some examples, the apparatus comprises a water pressure sensor configured to measure water pressure and to generate a depth signal indicating a depth of the apparatus in a body of water into which the apparatus is submerged. In those examples, the apparatus may be configured to detect a drowning situation (e.g., sinking) when the depth of the apparatus exceeds a predetermined depth and the acceleration signal matches a neutral acceleration signature during the same time period.

In some examples, the apparatus comprises an ambient temperature sensor configured to measure ambient temperature and to generate ambient temperature signals indicating the measured ambient temperature. In those examples, the apparatus may be configured to determine that the ambient temperature has exceeded an upper ambient temperature threshold for a predetermined time period and generate an over-temperature alert in response to a determination of that condition; and/or to determine that the ambient temperature has fallen below a lower ambient temperature threshold for a predetermined time period and generate an under-temperature alert in response to a determination of that condition.

In some examples, the apparatus may comprise a body temperature sensor configured to measure the body temperature of a user carrying the apparatus and generate a body temperature signal indicating such a measurement. In some examples, the apparatus may be configured to detect that the body temperature of the user, as indicated by the body temperature signal, exceeds a predetermined upper-limit body temperature and to generate a hyperthermia alert when such an event is detected. In other examples, the apparatus may be configured to detect that the body temperature of the user, as indicated by the body temperature signal, drops below a predetermined lower-limit body temperature and to generate a hypothermia alert when such an event is detected.

In some examples, the apparatus may comprise a heart rate sensor configured to measure the heart rate of a user carrying the apparatus and generate a heart rate signal indicating such a measurement. In those examples, the apparatus may be configured to detect that the heart rate of the user, as indicated by the heart rate signal, exceeds a predetermined upper-limit heart rate and to generate an over-heart-rate alert when such an event is detected. In those examples, the apparatus may be configured to detect that the heart rate of the user, as indicated by the heart rate signal, falls below a predetermined lower-limit heart rate and to generate a low-heart-rate alert when such an event is detected. In some examples, the apparatus may comprise a barometer configured to measure atmospheric pressure of the environment the apparatus is exposed to.

Another aspect of the disclosure relates to generating notifications based on various situations detected by multiple of the apparatus described above. The alerts generated by the apparatus as described above may be wirelessly transmitted to a server for further processing and/or management. The server may be configured to communicate with the client devices associated with the apparatuses. The server may intelligently determine, based on predetermined rules, whether a notification should be generated based on the reception of one or more alerts from a given apparatus. For example, the server may be configured to determine whether an abduction notification should be generated and transmitted to a client device associated with the given apparatus for presentation when an abduction alert is received from the given apparatus. For instance, the server may be configured to determine that the number of times such an alert is received from the given apparatus within a predetermined period has exceeded a predetermined threshold, and to generate an abduction notification to the client device associated with the given apparatus when such an event is determined by the server. As another illustration, the server may be configured to receive user preferences regarding the generation of the notifications when the signals and/or alerts are received from the apparatuses.

Still another aspect of the disclosure relates to tracking the apparatus described above. In one embodiment, the client device is facilitated to track multiple of the apparatus described above as a group. In that embodiment, a notification or alert regarding the group may be presented on the client device. For example, the client device may be facilitated to track locations of a group of the apparatuses and present an alert when one or more of the apparatuses in the group are outside an area or in close proximity to a restricted location.

These and other features and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
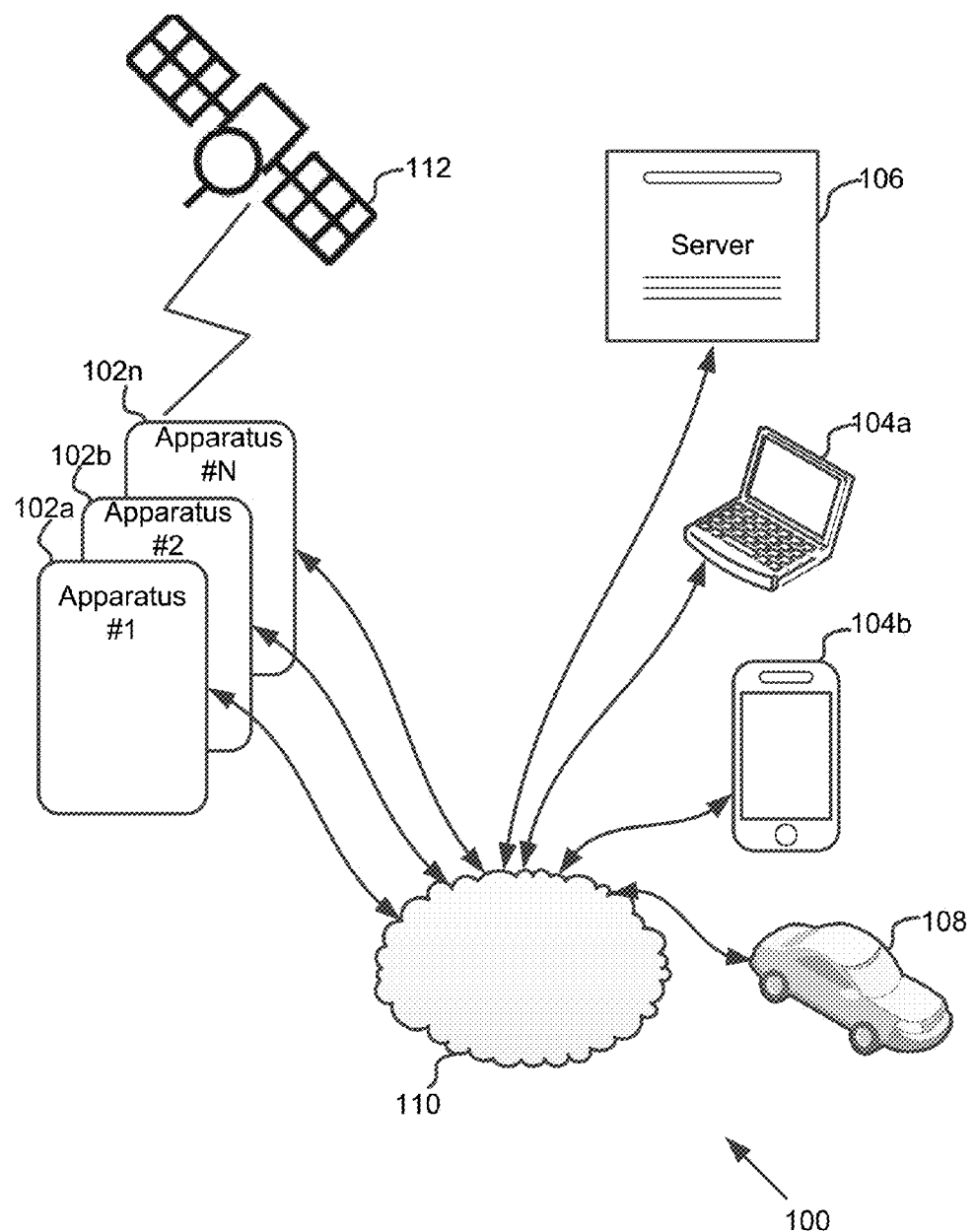
FIG. 1 generally illustrates one exemplary system facilitating personal tracking via an apparatus in accordance with the disclosure.

FIG. 1 generally illustrates an exemplary system 100 configured for facilitating personal tracking via an apparatus in accordance with the disclosure. As shown in FIG. 1, individual apparatuses 102 may be configured to communicate with client devices 104, a server 106, a vehicle 108 and/or any other entity associated with the apparatuses 102 via a communications network 110. A portion of, or the entire communications network 110, may include a wireless communication channel such as, but not limited to, Radio, Cellular (e.g., LTE), Bluetooth, WIFI, Infrared Laser, and/or any other type of wireless communication channel. As also shown, the apparatuses 102 may be configured to communicate with one or more of a location facility such as the satellite 112 shown in FIG. 1 or a reference station (not shown) that provides reference information for improving the accuracy of location determination to acquire location signals relating to the locations of the apparatuses 102.

The apparatuses 102 such as the apparatuses 102a, b and n shown in FIG. 1 may comprise multiple sensors configured to detect events or changes in an environment that the apparatuses 102 are exposed to. The sensors may include a water sensor, an ambient temperature sensor, an accelerometer, a water pressure sensor, a body temperature sensor, a heart-rate sensor, a barometer, and/or any other sensors. The apparatuses 102 may be configured to generate alerts regarding various situations encountered by the users carrying the apparatuses 102. The alerts generated by a given apparatus 102 may include a drowning alert, a wandering alert, an abduction alert, an over-temperature alert, an under-temperature alert, a heart-rate alert, a body temperature alert (e.g., a hyperthermia alert or a hypothermia alert), and/or any other alerts. In one embodiment, the apparatus 102 is a wearable device that may be worn by the user, for example, on his/her wrist, ankle, waist, or neck, or clipped to or inside the clothing of the user. However, this is not necessarily the only case. Other designs of apparatus 102, such as a portable device or a device that can be attached to the user's clothing, are contemplated.

The client devices 104, such as client devices 104a-b shown in FIG. 1, may be associated with the individual apparatuses 102 such that the alerts generated by the individual apparatuses 102 may be processed and/or presented by the corresponding client devices 104. Examples of a client device 104 may include a smart phone, a tablet, a hand-held device, a netbook, a laptop computer, a desktop computer, a display device, a television set, a monitor, and/or any other type of client device 104.

The server 106 may be configured to receive the alerts generated by the apparatuses 102, manage the individual apparatuses 102, manage user accounts of the users associated with the individual apparatuses 102, manage the alerts received from the apparatuses 102, generate notifications for presentation on the client devices 104 in response to the alerts received from the apparatuses 102, provide interfaces for users to access the alerts from the apparatuses 102 and/or perform any other operations. The server 106 may be configured to communicate with the client devices 104 associated with the apparatuses 102. The server 106 may intelligently determine, based on predetermined rules, whether a notification should be generated for presentation on the client devices 104 based on one or more alerts received from a given apparatus 102. For example, the server 106 may be configured to determine whether an abduction notification should be generated and transmitted to a client device 104 associated with the given apparatus for presentation when an abduction alert is received from the given apparatus 102. For instance, the server may be configured to determine that the number of times such an alert is received from the given apparatus 102 within a predetermined period has exceeded a predetermined threshold, and generate an abduction notification to the client device associated with the given apparatus 102 when such an event is determined by the server 106. As another illustration, the server 106 may be configured to receive user preferences regarding the generation of the notifications when the signals and/or alerts are received from the apparatuses 102. In one embodiment, the server 106 is a cloud server that provides online access to the status of the apparatuses 102, locations of the apparatuses 102, and alerts generated by the apparatuses 102.

Also shown in FIG. 1 is a vehicle 108, which may be configured to receive commands from the apparatuses 102, client devices 104, and/or server 106 in response to one or more of the alerts generated by apparatuses 102. The vehicle 108 may comprise a mechanism to perform one or more operations in response to the received commands. For example, the vehicle 108 may comprise a micro-processor configured to receive an "open window" command from the client device 104b via the network 110 in response to an over-temperature alert generated by the apparatus 102a. In response to the reception of the "open window" command, the micro-processor in the vehicle 108 may effectuate the performance the "open window" operation by issuing an instruction to a window actuator or the power window system of the vehicle instructing it to open the window of the vehicle 108.

Figure 2:
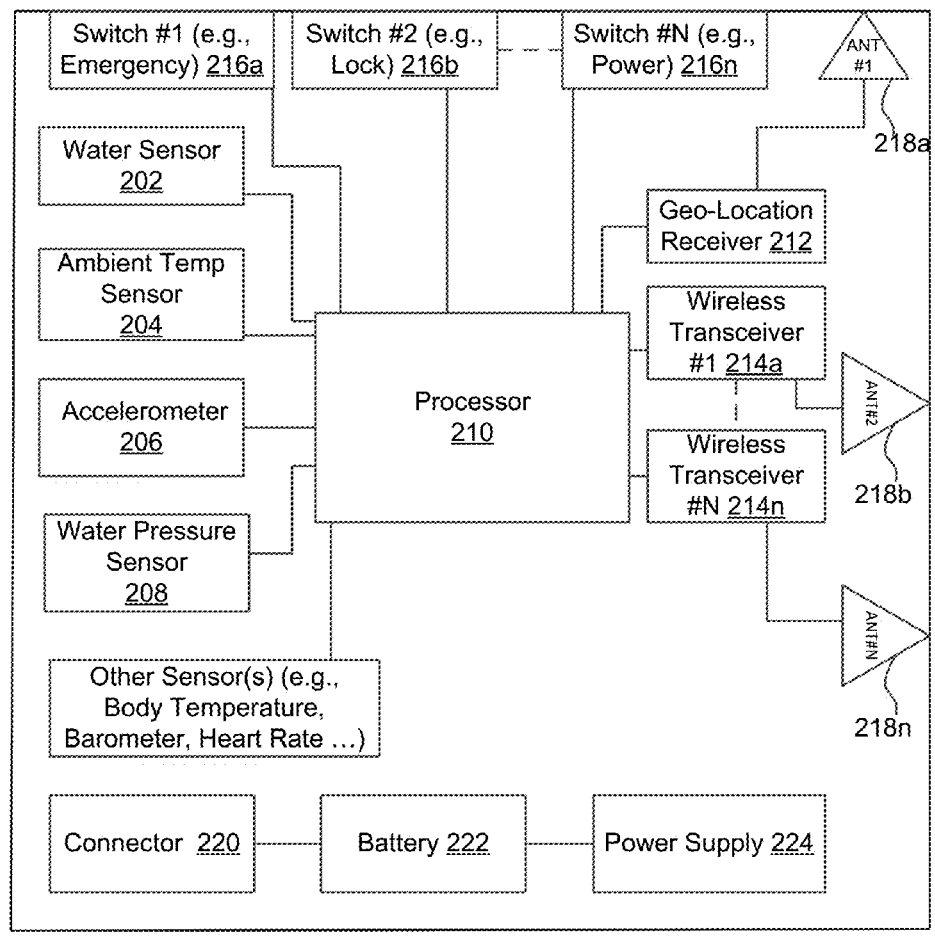
FIG. 2 illustrates one example of the apparatus shown in FIG. 1 in accordance with the disclosure.

With the system 100 having been generally described, attention is now directed to FIG. 2. FIG. 2 illustrates one example of the apparatus 102 in accordance with the disclosure. In this example, the apparatus 102 is a wearable device that may be worn by a user on his/her wrist. As shown, the apparatus 102 may comprise multiple sensors coupled to the processor 210 such as water sensor 202, ambient temperature sensor 204, accelerometer 206, water pressure sensor 208, and/or any other sensors (e.g., heart-rate sensor, body temperature sensor, barometer, etc.).

Figure 3B:
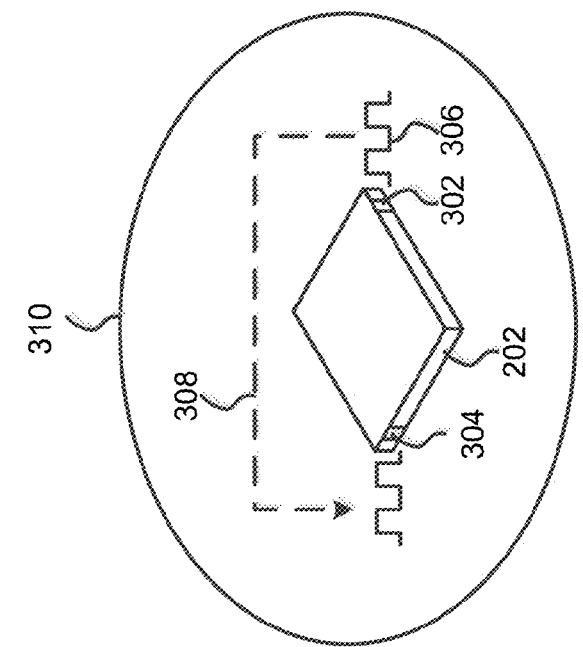
FIG. 3B illustrates a submersion signal is generated by the exemplary water sensor as shown in FIG. 2 when the water sensor is submerged into a body of water.
Figure 3A:
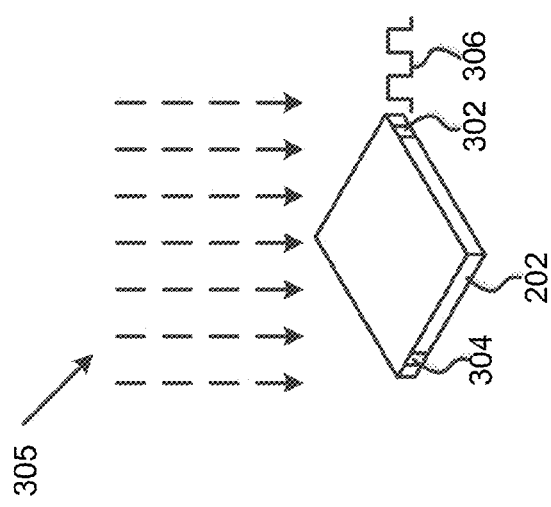
FIG. 3A illustrates a submersion signal is not generated by an exemplary water sensor as shown in FIG. 2 when the water sensor is partially exposed to water.

The water sensor 202 may be configured to generate a submersion signal by using the basic conduction property of water. In some examples, the water sensor 202 consists of two electrical contacts and the water submersion signal is generated when a conductive path is provided between the two electrical contacts. FIGS. 3A-B illustrate one example of the water sensor 202 comprising a first electrical contact 302 and a second electrical contact 304 in accordance with the disclosure. At the first contact 302, an electrical pulse 306 may be transmitted periodically. As shown in FIG. 3A, when the sensor 202 is exposed to rain 305, partially exposed to water or no water at all, a conductive path is not established between the first electrical contact 302 and the second electrical contact 304. In that situation, the electrical pulse 306 cannot be received at the second electrical contact 304 since there is no conductive path between the two electrical contacts. As shown in FIG. 3B, when the sensor 202 is submerged in a body of water 310, the conductive path 308 between the first electrical contact 302 and the second electrical contact 304 is established, and the electrical pulse 306 is received at the second electrical contact via the path 308. The water sensor 202 may be configured to generate a submersion signal when the electrical pulse is detected at the second electrical contact 304. The water sensor 202 may be configured to send the submersion signal to the processor 210 when the submersion signal is generated.

Returning to FIG. 2, the ambient temperature sensor 204 may be configured to measure ambient temperature and to generate signals reflecting the measured ambient temperature. In one embodiment, without limitation, the ambient temperature sensor 204 used in the apparatus 102 is TMP102 from Texas Instruments. In that embodiment, on sensing abnormal temperatures (too high or too low), the ambient temperature sensor 204 sends an alert signal to the processor 210.

Figure 4:
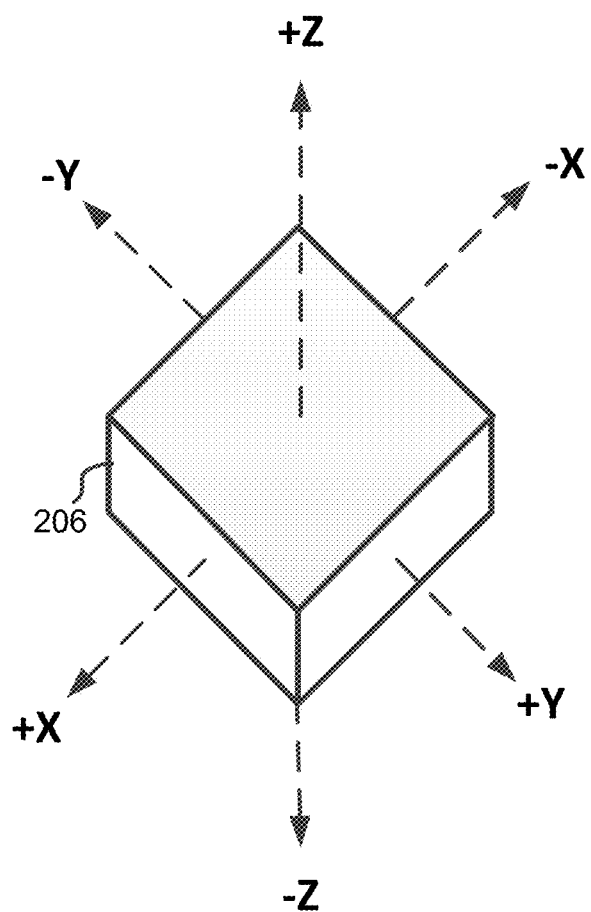
FIG. 4 illustrates one example of an accelerometer shown in FIG. 2.

The accelerometer 206 may be configured to measure acceleration of the apparatus 102 and to generate an acceleration signal reflecting the measured acceleration. The accelerometer 206 may be configured to measure translational accelerations and/or the rotational accelerations of the apparatus 102. FIG. 4 illustrates one example of accelerometer 206 in accordance with the disclosure. As shown, translational accelerations in X, Y, and Z directions may be measured by the accelerometer 206 in that example. In one embodiment, without limitation, the accelerometer 206 used in the apparatus 102 is MMA7660FC from Freescale.

Returning to FIG. 2, the water pressure sensor 208 may be configured to measure water pressure and to generate a depth signal based on the measured water pressure. In some examples, the water pressure sensor 208 includes a mechanical gauge. In some examples, the water pressure sensor 208 includes a pressure transducer such as a piezoresistive silicon transducer and is configured to measure water pressure by detecting a change in resistance of the resistors on the silicon die of the transducer.

It should be understood that the various sensors described above as being included in the exemplary apparatus 102 shown FIG. 2 are not intended to be limiting. In some other examples, the apparatus 102 may include greater or fewer sensors than those shown in FIG. 2. For example, the apparatus 102 may not include ambient temperature sensor 204 in some implementations. For example, the apparatus 102 may include a body temperature sensor configured to measure a body temperature of a user carrying the apparatus 102, a heart rate sensor configured to measure a heart rate of the user carrying the apparatus 102 and to generate a heart rate signal indicating such measurement, a barometer configured to measure atmospheric pressure of the environment the apparatus is exposed to and/or any other sensors that are not illustrated in FIG. 2.

The geo-location receiver 212 may be configured to receive geo-location signals from a location facility such as the satellite 112 shown FIG. 1 and to process the received geo-location signals. As shown, the geo-location receiver 212 may receive the geo-location signals via the antenna 218a included in apparatus 102. In some examples, the geo-location receiver 212 may be configured to determine geo-location coordinates indicating the location of the apparatus based on the received geo-location signals and to provide the determined geo-location coordinates to the processor unit 210 for further processing. In one embodiment, without limitation, the geo-location receiver 212 used in the apparatus 102 is SIM908 from SIMCOM.

Figure 5:
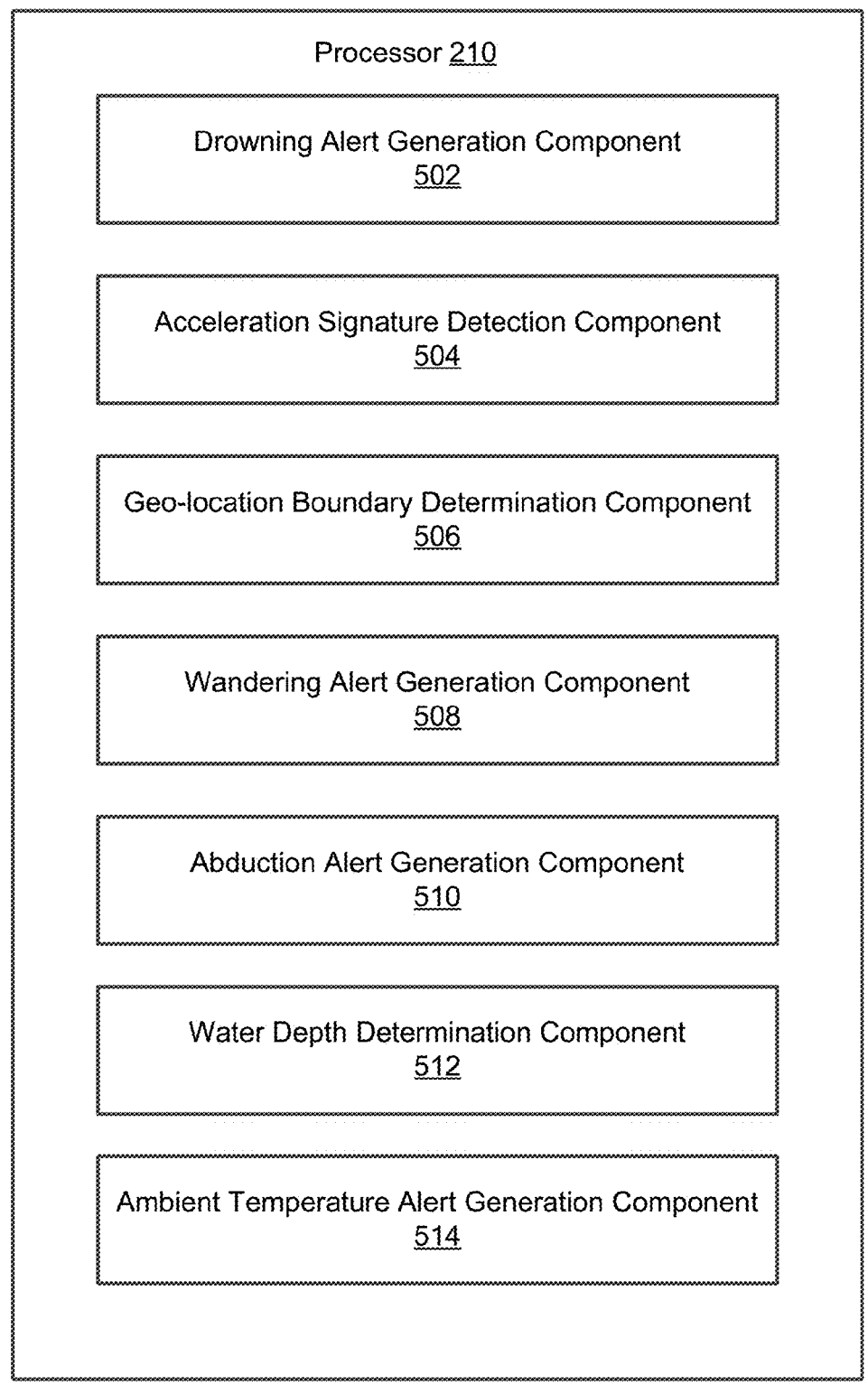
FIG. 5 illustrates one exemplary configuration of the processor shown in FIG. 2.

The processor 210 may be configured to implement one or more program components such that the processor 210 may receive signals from the various sensors described above and generate alerts based on the received signals. In one embodiment, without limitation, the processor 210 used in the apparatus is tSTM32F051R4T6 from STMicroelectronics. FIG. 5 illustrates one exemplary configuration of the processor 210. It will be described with reference to FIGS. 1-4. As shown in FIG. 5, the modules implemented by the processor 210 may include a drowning alert generation component 502, an acceleration signature detection component 504, a geo-location boundary determination component 506, a wandering alert generation component 508, an abduction alert generation component 510, a water depth determination component 512, a ambient temperature alert generation component 514, and/or any other components.

The drowning alert generation component 502 may be configured to generate a drowning alert based on the submersion signal generated by the water sensor 202, the acceleration signal generated by the accelerometer 204, and/or any other signals. In implementations, the drowning alert generation component 502 may be configured to receive, periodically or non-periodically, the submersion signals from the water sensor 202, the acceleration signals from the accelerometer 204, and/or any other signals. In some examples, the drowning alert generation component 502 may be configured to determine that drowning signature is matched based on the acceleration of the apparatus 102 as indicated by the acceleration signals when the submersion signal is received. For instance, the drowning alert generation component 502 may be configured to obtain one or more predetermined drowning signatures from an electronic storage coupled to the processor 210, compare the acceleration of the apparatus 102 within a time period with the one or more drowning signatures, and determine that an acceleration signature is matched if the acceleration of the apparatus 102 within the time period matches one of the one or more predetermined drowning signatures. In those examples, the drowning alert generation component 502 may be configured to detect that a drowning situation has occurred in response to the determination that the drowning signature is matched, and generate a drowning alert in response to the detection of the drowning situation.

Figure 6:
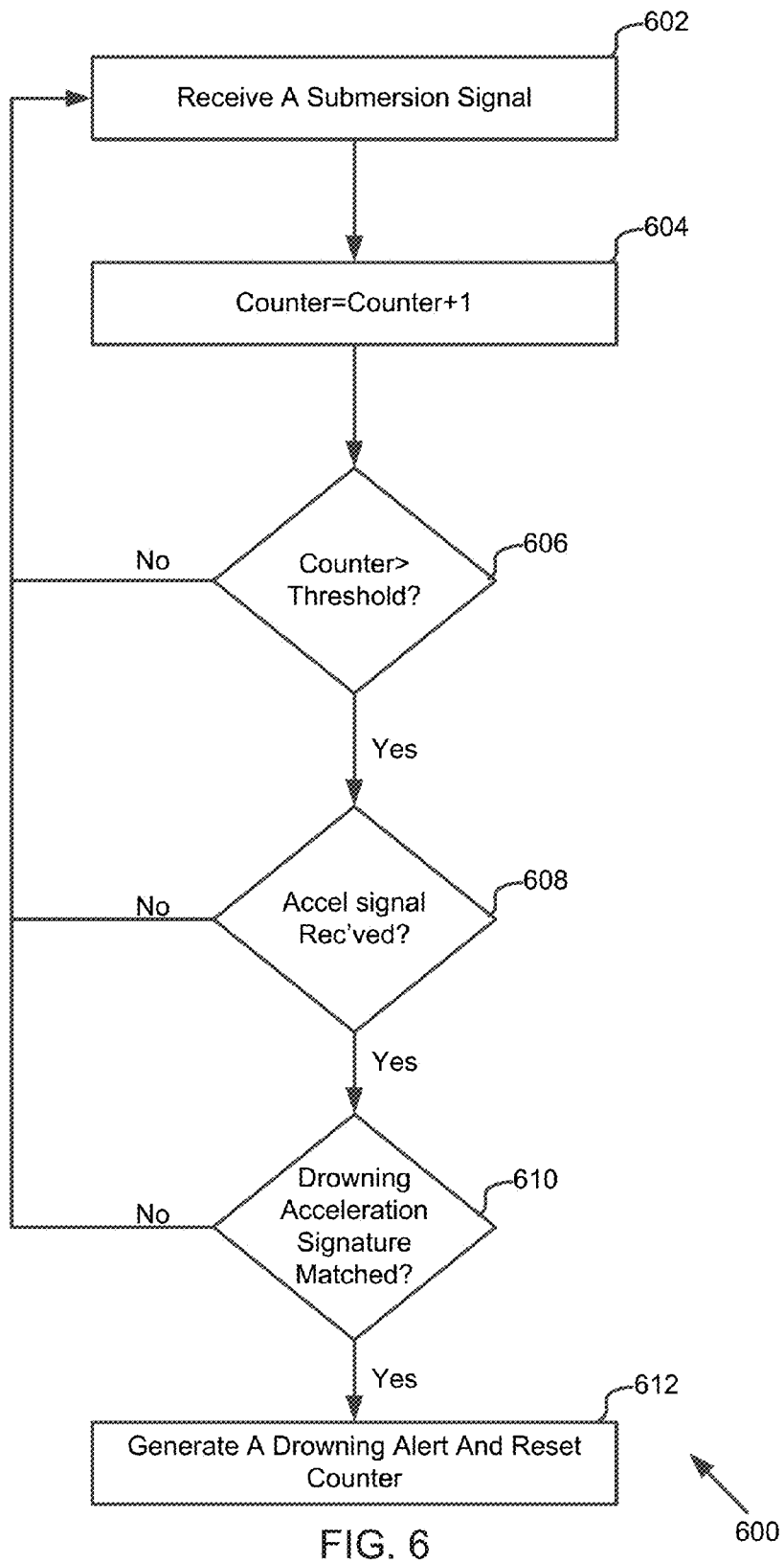
FIG. 6 illustrates an exemplary process for generating a drowning alert.

FIG. 6 illustrates an exemplary process 600 for generating a drowning alert. The operations of method 600 presented below are intended to be illustrative. In some embodiments, method 600 may be accomplished with one or more additional operations not described and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, a submersion signal may be received. As described above, the submersion signal may be generated by a water sensor such as the water sensor 202 when the apparatus 102 is submerged into a body of water. In some implementations, operation 602 may be performed by a drowning alert generation component the same as or substantially similar to the drowning alert generation component 502 described and illustrated herein.

At an operation 604, a counter may be incremented to keep a track of the number of times the submersion signal is received within a time period. For example, the counter may be used to keep a track of the number of times the submersion signal is received within a 5 second, 10 second, 30 second, or any other time period. Initially the counter may be set to 0 at the beginning of the time period. Every time when the submersion signal is received at operation 602 during the time period, the counter may be incremented by 1 at operation 604. In some implementations, operation 604 may be performed by a drowning alert generation component the same as or substantially similar to the drowning alert generation component 502 described and illustrated herein.

At a decision 606, the value of the counter is compared with a threshold value. The threshold value may be preconfigured by the user (e.g., a parent), manufacturer, an administrator, a safety personnel and/or any other entity related to the apparatus 102. In some examples, the client device 104 associated with the apparatus 102 may include an input means and an interface for setting various configurations of the apparatus 102 including the threshold value used by the decision 606. For example, the threshold value may be set to 10 from the client device 104. As shown, in the case where the counter value has not exceeded the threshold value as determined by decision 606, the process 600 proceeds back to operation 602; and in the case where the counter value has exceeded the threshold value, the process 600 proceeds to decision 608. In some implementations, operation 606 may be performed by a drowning alert generation component the same as or substantially similar to the drowning alert generation component 502 described and illustrated herein.

At decision 608, it is determined whether an acceleration signal is received in the same time period during which the number of submersion signals received has exceeded the threshold value as determined by decision 606. As shown, in the case where it is determined that the acceleration signal is received during the same time period, which indicates the apparatus is accelerating during the same time period, the process 600 proceeds to decision 610; and in the case where it is determined that the acceleration signal is not received during the same time period, the process proceeds back to operation 602. In some implementations, decision 608 may be performed by a drowning alert generation component the same as or substantially similar to the drowning alert generation component 502 described and illustrated herein.

At decision 610, a determination whether a drowning acceleration signature is matched by the acceleration of the apparatus 102 may be made after it is determined that the number of submersion signals received during the time period has exceeded the preset threshold value and at least an acceleration signal is received during that time period. In implementations, decision 610 may involve obtaining one or more stored drowning acceleration signatures from an electronic storage included in or coupled to the apparatus 102, such as flash memory. The one or more drowning signatures may be set and stored by a user (e.g., a parent), the manufacturer of the apparatus 102, an administrator of a safety standards body or service provider, and/or any other entity related to the apparatus 102. A given one of the stored drowning signatures may indicate an acceleration pattern that indicates a drowning situation may have occurred. For example, without limitation, the given stored drowning signature may indicate an acceleration pattern in a right-left-down-right-left-right sequence within a span of a 5 second time period, an acceleration pattern involving 3 translational accelerations and 2 rotational accelerations within a span of 3 seconds, or any other acceleration pattern indicating quick movements within a short time period which may indicate the user carrying the apparatus 102 is thrashing.

The decision 610 may involve operation(s) of comparing the acceleration signal(s) received during the time period with the one or more stored drowning signatures. For example, an acceleration pattern of the apparatus within the time period may be determined from the acceleration signal(s) received during the time period. As illustrated in FIG. 4, the acceleration signal(s) received during the time period may reflect acceleration by the apparatus 102 in translational and/or rotational directions during the time period. For example, the acceleration signals may be in the form of voltages corresponding to X, Y, and Z axes and based on such, acceleration by the apparatus 102 may be determined. The determined acceleration pattern may then be compared with the one or more stored drowning signatures. As shown in FIG. 6, in the case where a drowning acceleration signature is matched, the process proceeds to operation 612, and in the case where a drowning acceleration signature is not matched, the process proceeds back to operation 602. In some implementations, decision 610 may be performed by a drowning alert generation component the same as or substantially similar to the drowning alert generation component 502 described and illustrated herein.

At operation 612, a drowning alert is generated in response to the drowning acceleration signature being matched at decision 610. Also at operation 612, the counter is reset to 0. In some implementations, operation 612 may be performed by a drowning alert generation component the same as or substantially similar to the drowning alert generation component 502 described and illustrated herein.

The process 600 described above provides a way to detect a drowning situation when both submersion signal(s) and acceleration signal(s) are received during the same time period. In the case where a submersion signal is not received or is received fewer times than the preset threshold number of times during the time period, a drowning alert is not generated regardless whether the acceleration signal(s) is received during the same time period. This may avoid a false drowning alert when the user carrying the apparatus 102 is only partially exposed to water, e.g., playing with a bucket of water or in the rain. In some examples, a water alert is generated by the drowning alert generation component 502 when submersion signals are received more times than the preset threshold number of times during the time period. The water alert may be generated to indicate that the user carrying the apparatus 102 is in the water but no drowning is detected yet. This may be useful to alert the parent to be cautious that the child carrying the apparatus may be in potential danger of drowning or other water related hazards since the child is being exposed to water.

Returning to FIG. 5, the acceleration signature detection component 504 may be configured to detect an acceleration signature based on the acceleration signal. The acceleration signatures detected by the acceleration signature detection component 504 may include the drowning signature described above and herein, an abduction acceleration signature, a neutral acceleration signature, and/or any other acceleration signatures. The abduction acceleration signature may be detected by the acceleration signature detection component 504 when the acceleration by the apparatus 102 as indicated by the acceleration signal(s) received from the accelerometer 206 matches at least one of one or more predefined abduction acceleration signatures. The one or more predefined abduction acceleration signatures may be predefined by the user (e.g., a parent), the manufacturer of apparatus 102, an administrator of a safety standard body or service provider, and/or any other entity related to apparatus 102. The predefined one or more abduction acceleration signatures may be stored in an electronic storage component included in or coupled to the apparatus 102, such as a flash memory. A given one of the predefined abduction acceleration signatures may reflect an acceleration pattern typical of an abduction situation. For example, such an abduction acceleration signature may specify an acceleration pattern of abrupt direction changes over a threshold number of times (e.g., 20 times) in a short time period (e.g., in one minute), which may indicate that the user carrying apparatus 102 is struggling with the abductor(s). As another example, such an abduction acceleration signature may specify an acceleration pattern of abrupt direction changes over a threshold number of times with average acceleration during that period over an upper limit and followed by no acceleration during the next time period, which may indicate the abductor(s) may have taken control of the user carrying the apparatus 102 after the struggle. As another example, a predefined abduction acceleration signature may reflect an acceleration and/or velocity pattern that is associated with a vehicle leaving an abduction location (e.g., rapid acceleration and high velocity).

The neutral acceleration signature may be detected by the acceleration signature detection component 504 when the acceleration by the apparatus 102 as indicated by the acceleration signal(s) received from the accelerometer 206 matches at least one of one or more predefined neutral acceleration signatures. The one or more predefined neutral acceleration signatures may be predefined by the user (e.g., a parent), the manufacturer of apparatus 102, an administrator of a safety standard body or service provider, and/or any other entity related to apparatus 102. The predefined one or more neutral acceleration signatures may be stored in an electronic storage component included in or coupled to the apparatus 102, such as a flash memory. A given one of the predefined neutral acceleration signatures may reflect an acceleration pattern typical of a neutral (normal or expected) acceleration situation, such as walking, running, biking or riding in a vehicle. For example, such a neutral acceleration signature may specify an acceleration pattern of an average acceleration during a time period when the user carrying the apparatus 102 starts running.

The water depth determination component 512 may be configured to determine whether the depth of the apparatus 102 exceeds a predetermined depth in a body of water when the submersion signal is received. In implementations, the water depth determination component 512 may be configured to receive the depth signal from the water pressure sensor 208 and determine the depth of the apparatus 102 in the body of water based on the depth signal.

Figure 7:
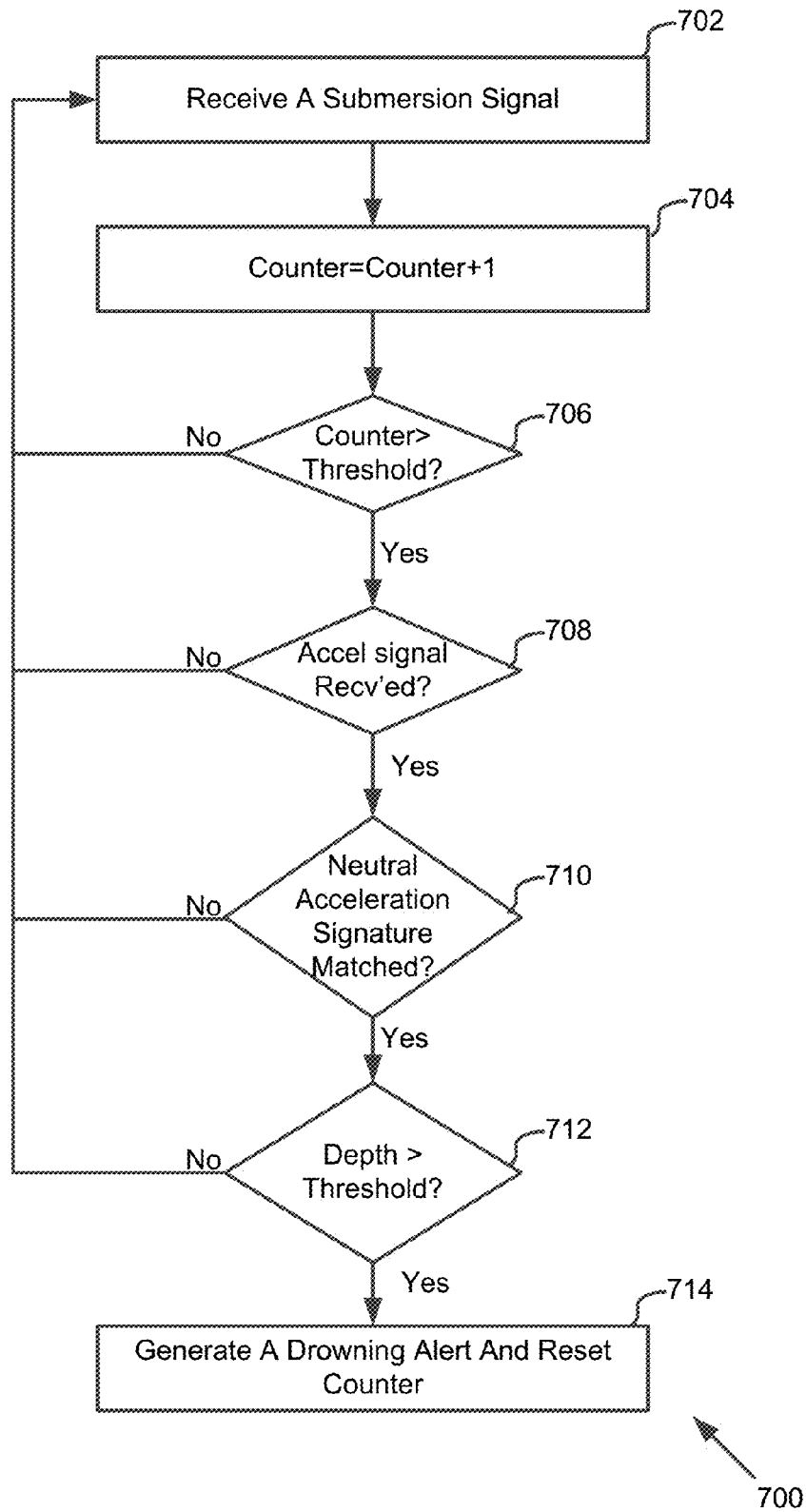
FIG. 7 illustrates another exemplary process for generating a drowning alert.

FIG. 7 illustrates an exemplary process 700 for generating a drowning alert. Process 700 is similar to process 600 except that it takes into account the depth of the apparatus 102 when generating the drowning alert. In the interest of brevity, FIG. 7 will be described with respect to the differences from process 600 illustrated in FIG. 6, which are decisions 710 and 712. As shown, at decision 710, a determination may be made whether a neutral acceleration signature is matched after it is determined that the number of submersion signals received during the time period has exceeded the preset threshold value and at least an acceleration signal is received during the time period. In some implementations, decision 710 may be implemented by an acceleration signature generation component the same as or substantially similar to the acceleration signature generation component 504 as described herein. At decision 712, it may be determined whether the depth of apparatus 102 has exceeded a predetermined depth threshold (e.g., 6 feet into the water) during the same time period that the acceleration signature is detected. In some implementations, decision 712 may be implemented by a water depth determination component the same as or substantially similar to the water depth determination component 512 as described herein. The process 700 provides a way to detect a drowning situation when the user is sinking in the water without thrashing (which may indicate that the user is unconscious, for example) and generate a drowning alert accordingly to indicate the user carrying the apparatus 102 may be sinking in the body of water. This may be useful when a child is swimming in a lake or pond, and is temporarily out of sight of his/her parent(s).

Returning to FIG. 5, the geo-location boundary determination component 506 may be configured to determine whether the apparatus 102 is outside the boundaries of one or more predefined geographical areas. This may involve receiving location boundary information for boundaries of one or more areas. For example, the geo-location boundary determination component 506 may be configured to receive such information from the client device 104 associated with the apparatus 102, from the server 106, and/or from any other components. As illustration, without limitation, the user of the client device 104, e.g., a parent, may set the boundaries of geo-location area(s) in which the parent wants his/her child (i.e., the user carrying the apparatus 102) to remain. The geo-location boundary determination component 506 may receive such information from the client device 104 during a configuration stage of the apparatus 102 or dynamically when the parent wishes to set the boundaries from the client device 104. The determination whether the apparatus 102 is outside the boundaries by the geo-location boundary determination component 506 may involve comparing the location coordinates provided by the geo-location receiver 212 with the received boundary information periodically. In the event when the geo-location boundary determination component 506 detects the location coordinates are outside the perimeters of the boundaries of the one or more areas, the geo-location boundary determination component 506 may be configured to generate an out-of-boundary alert to indicate such.

The wandering alert generation component 508 may be configured to generate a wandering alert when the apparatus 102 is determined to be outside/inside the boundaries of the one or more geo-location areas and a neutral acceleration signature is detected in the same time period. In some implementations, the wandering alert generation component 508 may be configured to monitor whether an out-of-boundary alert is generated by the geo-location boundary determination component 506. In the event when the out-of-boundary alert is generated by the geo-location boundary determination component 506, the wandering alert generation component 508 may be configured to poll the acceleration signature generation component 504 to determine whether a neutral acceleration signature (e.g., a neutral acceleration signature indicating the user carrying the apparatus 102 is walking, running or biking) is matched. In the event when such a neutral acceleration signature is detected, the wandering alert generation component 508 may be configured to generate the wandering alert. This may be useful to avoid a false alert when a child carrying the apparatus 102 is only temporarily out of the preset boundaries, and to generate a wandering alert when the child is out of the boundaries with neutral acceleration over a predetermined time period. In some implementations, the wandering alert generation component 508 may be configured to monitor whether a user carrying apparatus 102 is inside boundaries of one or more restricted areas, such as lakes or railway tracks, and generate a wandering alert when such an event is detected in the same time period during which a neutral acceleration signature is matched.

The abduction alert generation component 510 may be configured to generate an abduction alert when the apparatus 102 is determined to be outside the boundary of the one or more areas and an abduction acceleration signature is detected in the same time period. In some implementations, the abduction alert generation component 510 may be configured to monitor whether an out-of-boundary alert is generated by the geo-location boundary determination component 506. In the event when the out-of-boundary alert is generated by the geo-location boundary determination component 506, the abduction alert generation component 510 may be configured to poll the acceleration signature generation component 504 to determine whether an abduction acceleration signature is matched. In the event when an abduction acceleration signature is detected, the abduction alert generation component 510 may be configured to generate the abduction alert. This may be useful to avoid a false alert when a child carrying the apparatus 102 is only temporarily out of the preset boundaries, and to generate an abduction alert when the child is going out of the boundaries with acceleration indicating an abduction situation over a predetermined time period.

Figure 8:
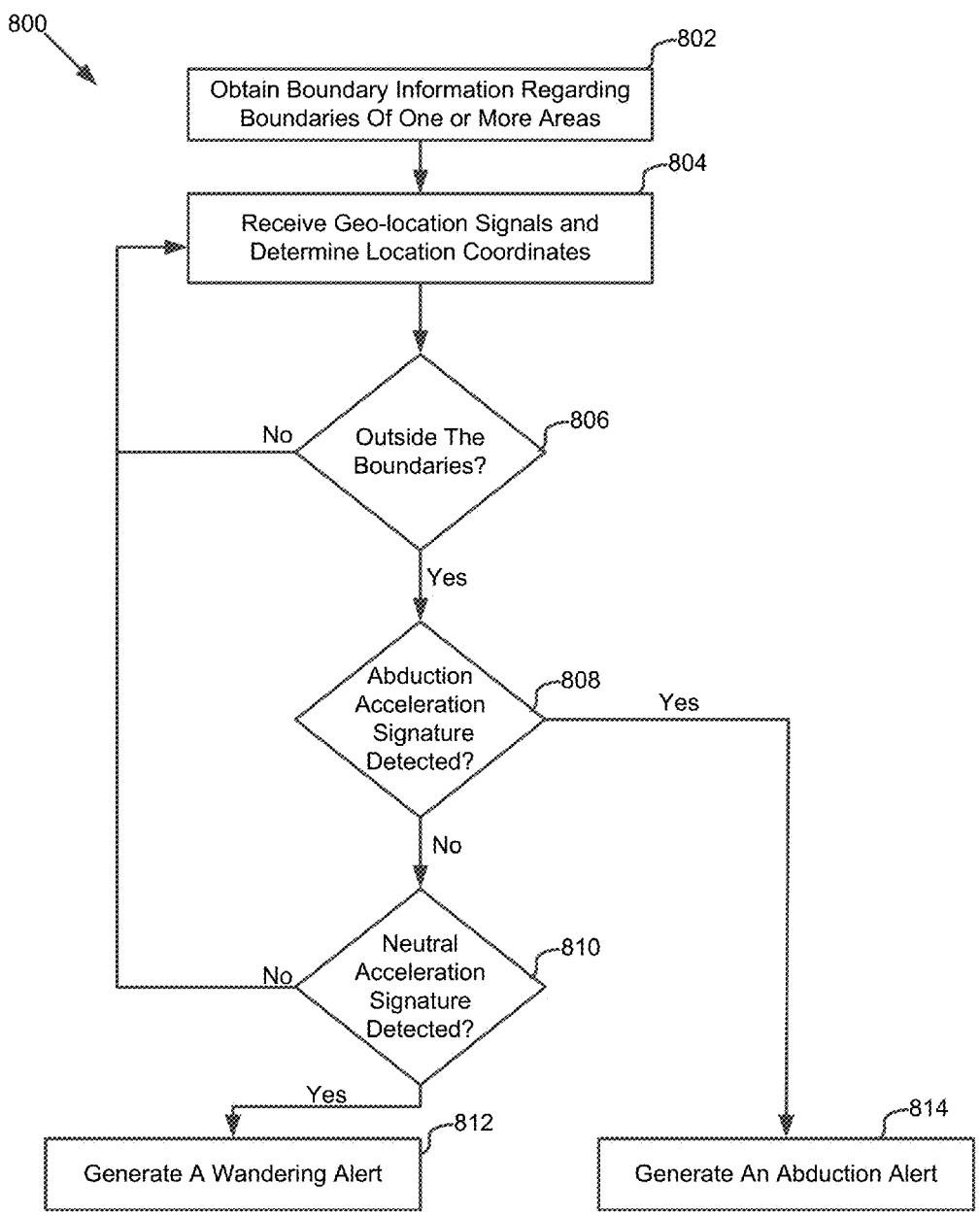
FIG. 8 illustrates a flow diagram of one exemplary process for generating a wandering alert and an abduction alert in accordance with the disclosure.

FIG. 8 illustrates a flow diagram of one exemplary process for generating a wandering alert and an abduction alert in accordance with the disclosure. The operations of method 800 presented below are intended to be illustrative. In some embodiments, method 800 may be accomplished with one or more additional operations not described and/or without one or more of the operations discussed. Additionally, the order in which the operations of method 800 are illustrated in FIG. 5 and described below is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, boundary information regarding boundaries of one or more areas may be received. As described herein, the boundary information may be received from the client device 104 associated with the apparatus 102, from the server 106, and/or from any other component. In some implementations, operation 802 may be performed by a geo-location boundary determination component the same as or substantially similar to the geo-location boundary determination component 506 described and illustrated herein.

At an operation 804, location coordinates may be determined based on geo-location signals received from a geo-location receiver such as the geo-location receiver 212. In some implementations, operation 804 may be performed by a geo-location boundary determination component the same as or substantially similar to the geo-location boundary determination component 506 described and illustrated herein.

At decision 806, a determination may be made whether the location of the apparatus is outside the boundaries of the one or more areas by comparing the location coordinates determined at operation 804 with the boundary information received at operation 802. In some implementations, operation 806 may be performed by a geo-location boundary determination component the same as or substantially similar to the geo-location boundary determination component 506 described and illustrated herein.

At decision 808, a determination whether an abduction acceleration signature is detected may be made. As shown, in the case where it is determined that an abduction acceleration signature is detected, the process proceeds to operation 814 to generate an abduction acceleration alert; and in the case where it is determined that an abduction acceleration signature is not detected, the process proceeds to decision 810. In some implementations, operation 808 may be performed by an abduction alert generation component the same as or substantially similar to the abduction alert generation component 510 described and illustrated herein.

At decision 810, a determination whether a neutral acceleration signature is detected may be made. As shown, in the case where it is determined that a neutral acceleration signature is detected, the process proceeds to operation 812 to generate a wandering alert; and in the case where it is determined that a neutral acceleration signature is not detected, the process proceeds back to operation 804. In some implementations, operation 808 may be performed by a wandering alert generation component the same as or substantially similar to the wandering alert generation component 508 described and illustrated herein.

At operation 812, a wandering alert may be generated in response to the detection of a neutral acceleration signature at operation 810 and the determination that the apparatus 102 is out of the boundaries at 806 in the same time period. In some implementations, operation 812 may be performed by a wandering alert generation component the same as or substantially similar to the wandering alert generation component 508 described and illustrated herein.

At operation 814, an abduction alert may be generated in response to the detection of an abduction acceleration signature at operation 808 and the determination that the apparatus 102 is out of the boundaries at 806 in the same time period. In some implementations, operation 814 may be performed by an abduction alert generation component the same as or substantially similar to the abduction alert generation component 510 described and illustrated herein.

Returning to FIG. 5, the ambient temperature alert generation component 514 may be configured to determine whether the ambient temperature, as indicated by the ambient temperature signals, has exceeded an upper ambient temperature threshold for a predetermined time period. This may involve receiving the ambient temperature signal periodically from the ambient temperature sensor 204, determining the ambient temperature measurement from the ambient temperature signal, and comparing the measured ambient temperature with the upper ambient temperature threshold periodically. The upper ambient temperature threshold may be preset and stored by a user (e.g., a parent), the manufacturer of the apparatus 102, an administrator of a safety standards body or service provider, and/or any other entity related to the apparatus 102. The ambient temperature alert generation component 514 may be configured to generate an over-temperature alert in response to the determination that the ambient temperature has exceeded the upper ambient temperature threshold for the predetermined time period. For example, without limitation, the over-temperature alert may be generated when the measured ambient temperature has exceeded 110 degrees Fahrenheit for more than two minutes (threshold).

The ambient temperature alert generation component 514 may be configured to determine whether the ambient temperature, as indicated by the ambient temperature signals, has fallen below a lower ambient temperature threshold for a predetermined time period. This may involve comparing the measured ambient temperature with the lower ambient temperature threshold periodically. The lower ambient temperature threshold may be preset and stored by a user (e.g., a parent), the manufacturer of the apparatus 102, an administrator of a safety standards body or service provider, and/or any other entity related to the apparatus 102. The ambient temperature alert generation component 514 may be configured to generate an under-temperature alert in response to the determination that the ambient temperature has fallen below a lower ambient temperature threshold for the predetermined time period. For example, without limitation, the under-temperature alert may be generated when the measured ambient temperate has fallen below −30 degrees Fahrenheit for more than five minutes (threshold).

It should be appreciated that although components 502, 504, 506, 508, 510, 512, 514 are illustrated in FIG. 5 as being co-located within a single processing unit 210, in implementations in which processor 210 includes multiple processing units, one or more of components 502, 504, 506, 508, 510, 512, 514 may be located remotely from the other components. The description of the functionality provided by the different components 502, 504, 506, 508, 510, 512, 514 described herein is for illustrative purposes, and is not intended to be limiting, as any of components 502, 504, 506, 508, 510, 512, 514 may provide more or less functionality than is described. For example, one or more of components 502, 504, 506, 508, 510, 512, 514 may be eliminated, and some or all of its functionality may be provided by other ones of components 502, 504, 506, 508, 510, 512, 514. As another example, processor 128 may be configured to execute one or more additional components that may perform some or all of the functionality attributed below to one of components 502, 504, 506, 508, 510, 512, 514.

In some implementations, the processor 210 may be configured to detect that the body temperature of the user carrying apparatus 102, as indicated by the body temperature signal generated by a body temperature sensor included in the apparatus 102, exceeds a predetermined upper-limit body temperature and generate a hyperthermia alert when such an event is detected. In some implementations, the processor 210 may be configured to detect that the body temperature of the user carrying apparatus 102, as indicated by the body temperature signal generated by a body temperature sensor included in the apparatus 102, falls below a predetermined lower body temperature limit and generate a hypothermia alert when such an event is detected.

In some implementations, the processor 210 may be configured to detect that the heart rate of the user carrying the apparatus 102, as indicated by the heart rate signal generated by a heart-rate sensor included in the apparatus 102, exceeds a predetermined upper-limit heart rate and generate an over-heart-rate alert when such an event is detected. In those examples, the apparatus may be configured to detect that the heart rate of the user, as indicated by the heart rate signal, drops below a predetermined lower-limit heart rate and generate a low-heart-rate alert when such an event is detected.

Returning to FIG. 2, as shown the apparatus 102 may include one or more wireless transceivers 214 configured to transmit data from the apparatus 102 via corresponding antenna 218. The wireless transceivers 214 may include a WIFI, a Bluetooth, an LTE, a GSM, and/or any other wireless transceivers. As shown the wireless transceivers 214 may be coupled to the processor 210, which may be configured to effectuate transmission of various alerts generated by the processor 210 described above via the wireless transceivers 214.

As also shown, the apparatus 102 may include one or more switches 216 such as switches 216a, b and n. As shown in this example, without limitation, the switch 216a is an emergency assistance (SOS) button. When pressed, the switch 216a may cause the processor 210 to send an SMS alert to one or more predefined telephone numbers with the location of the apparatus 102 determined from the geo-location signals received by the geo-location receiver 212.

In this example, the switch 216b is a lock switch. When pressed, the switch 216b may cause the processor 210 to lock or unlock the hardware component of the apparatus 102. In one embodiment, without limitation, the client device 104 associated with the apparatus is enabled to lock the hardware component of the apparatus 102 by sending an SMS message containing a predefined lock code. Upon receiving the SMS message, the processor 210 may be configured to lock the hardware component of the apparatus 102. In that example, the switch 216b, when pressed, may unlock the hardware component of the apparatus 102.

In this example, the switch 216n is a power on/off switch. The switch 216n, when pressed, may cause the apparatus to power on or power off. Other examples of switches that may be included in the apparatus 102 and corresponding functionalities are contemplated. For example, a switch may be included in the apparatus 102 to cause the processor 210 to detect whether continuity of a circuit in the apparatus 102 is interrupted. For instance, that switch may be extended to a circuit in the apparatus 102 and when the apparatus 102 is forcefully removed from the user carrying the apparatus 102, that switch may automatically interrupt the circuitry to cause the processor 210 to generate a corresponding alert.

Also shown in FIG. 2 are a connector 220 for connection to an external charging source, a battery 222, and a power supply 224 to supply power to the apparatus 102. In one embodiment, without limitation, the battery 222 is a rechargeable 3.7V 1200 mAH Li-ion battery with a charging circuit such as a BQ24232 from Texas Instruments; and the power supply is a Buck-Boost converter TPS63021 from Texas Instruments.

With various components included in the apparatus 102 having been described, attention is now directed to the client device 104 shown in FIG. 1. As mentioned above, a client device 104 may be associated with one or more apparatuses 102. In some implementations, the client device 104 may be configured to receive alerts from the associated apparatus(es) 102 directly via the communications network 110 or from the server 106. In those implementations, the client device 104 may be configured to process the received alerts and present corresponding notifications to the user of client device 104 (e.g., a parent). For example, without limitation, the client device 104 may be configured to receive the drowning alert from the apparatus 102 and generate a notification such that a message indicating the user carrying the apparatus 102 may be drowning may be presented on the client device 104. For instance, such a notification may be in red, blinking with audible alert when presented on the client device 104. As another example, the client device 104 may be configured to receive the wandering alert from the apparatus 102 and generate a notification such that a message indicating the user carrying the apparatus 102 may be wandering outside the preset boundaries. For instance, such a notification may be presented in yellow text and may not be as conspicuous as the notification indicating the user carrying the apparatus 102 is drowning. Other examples of notifications that may be generated by the client device 104 in response to alerts being received from the apparatus 102 are contemplated.

Figure 9:
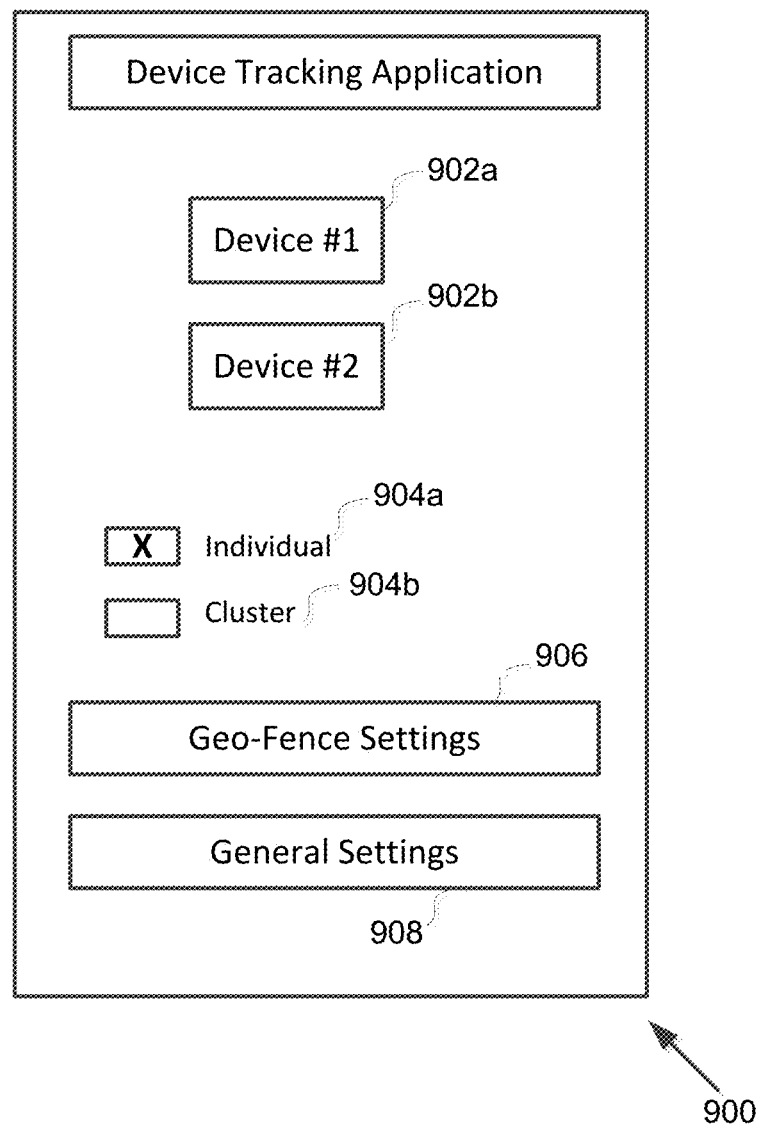
FIG. 9 illustrates one example of an interface provided by the client device shown in FIG. 1 for configuring the tracking and settings of the apparatus shown in FIG. 1.

In some implementations, the client device 104 may be configured to provide an interface for a user of the client device 104 (e.g., a parent) to configure the settings of the apparatus 102, the geo-location boundary information, specific apparatus 102 to be tracked and/or to perform any other operations related to the apparatus 102 associated with the client device 104. FIG. 9 illustrates one example of such an interface. As shown, the interface 900 may be provided on the client device 104. The interface 900 may comprise device information boxes 902 such as the boxes 902a-b shown in FIG. 9. Each device information box 902 may display an individual apparatus 102 that is associated with the client device 104. In this example, the client device 104 is associated with two apparatuses 102, i.e., device #1 and device #2. The user of client device 104 may be enabled to add more apparatuses to be associated with the client device 104 or remove one or more existing apparatuses 102 associated with the client device 104. In some implementations, when the user of the client device 104 presses one of the boxes 902 the location information of the corresponding apparatus may be transmitted to client device 104 for presentation.

In some implementations, a given apparatus 102 may be associated with more than one client device 104. In those implementations, interfaces 900 on the individual client devices associated with the given apparatus 102 enables the users of those client devices (e.g., parent, grandparent, teacher or any other caretaker of the child carrying apparatus 102) to configure the apparatus 102.

In some implementations, a given apparatus 102 may be associated with a primary client device 104 and one or more secondary client devices 104. In those implementations, alerts transmitted, either directly or via server 106, to the primary client device 104 from the given apparatus 102 may be stored and managed at server 106. It is contemplated that the interface 900 may include a control field or control fields (e.g., a button) that requires the user of the primary device 104 (e.g., a parent) to acknowledge the alerts presented on the primary client device 104 by acting on the control field(s) (e.g., pushing the button). It is contemplated that the primary client device 104 may be configured to effectuate transmission of the alerts from server 106 to the secondary client devices 104 associated with the given apparatus 102 when the user of the primary client device 104 fails to acknowledge the alerts (e.g., fails to push the button in the interface 900). It is contemplated that that the alerts may be transmitted to the secondary client devices 104 in a minute by minute log format for presentation to the alerts to the users of the secondary client devices 104.

Figure 10:
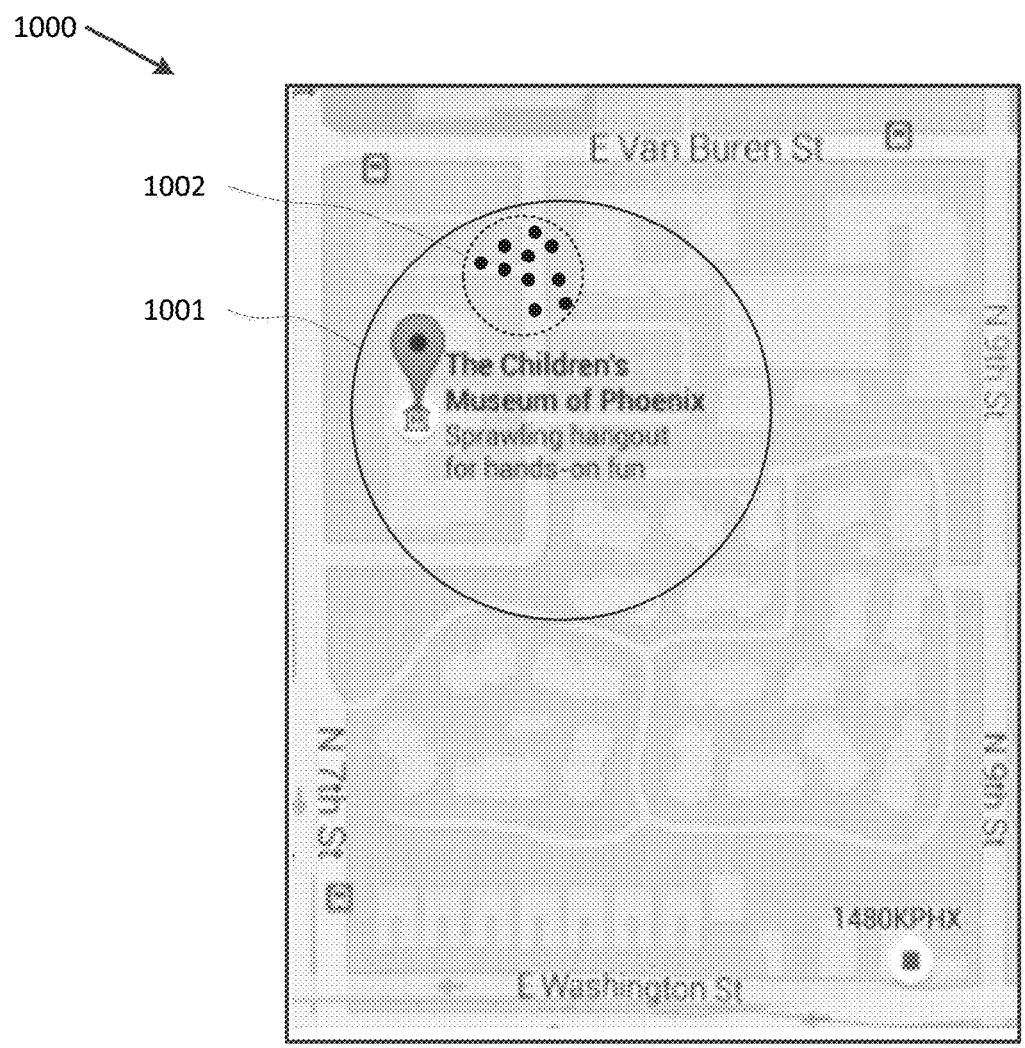
FIG. 10 illustrates an interface implemented on the client device shown in FIG. 1 enabling the user of the client device to monitor the users of apparatus associated with the client device as a group.

As also shown, the interface 900 may include a mode section enabling the user of client device 104 (e.g., a parent) to select a tracking mode. As shown, two tracking modes may be enabled by the interface 900. The individual tracking mode may enable the user of the client device 104 to track the apparatuses 102 associated with the client device 104 individually. For example, the user of the client device 104 may select this mode to receive individual alerts from the apparatuses 102 associated with the client device 104 and present notifications about the associated apparatus individually. The cluster tracking mode may enable the user of the client device 104 to track the apparatuses 102 associated with the client device 104 as a group. For example, in this mode, the client device 104 may receive alerts regarding the associated devices as a group. This may be useful when the users of the associated apparatuses 102 are engaging in a group activity. By way of example, this mode may enable a teacher (the user of the client 104) to monitor his/her students carrying the apparatuses 102 as a group 1002 and configure tracking settings such as a geo-fence for the group. FIG. 10 illustrates an interface 1000 implemented on the client device 104 enabling the user of the client device to monitor the users of apparatuses 102 associated with the client device 104 as a group. As shown, a geo-fence 1001 for the group may be readily visible on a map. The geo-fence 1001 may be defined by the user of the client device 104 via the geo-fence button 906 shown in FIG. 9, which, when the cluster mode is selected, is applicable to the entire group 1002 of apparatuses 102 associated with the client device 104. In implementations, individual apparatus 102 may be assigned a unique device identification number. To enable the cluster mode, the user of client device 104 may be prompted to enter these device identification numbers, so that they may be registered at the client device 104 or at the server 106. The registered device numbers may be mapped to user-defined names, for example the name of the user carrying apparatus 102, so that a notification such as "Ann out of geo-fence" can be alerted to the client device 104. Once the apparatuses 102 are registered, then the geo-fence with the location of the apparatuses 102 as a cluster can be viewed as shown in FIG. 10. In some implementations, the user of client device 104 may be enabled to provide a location where the users carrying the apparatuses 102 should not be near, such as electrical power lines, power stations, water tanks, and/or any other hazardous locations that may not be safe the users carrying the apparatuses 102. In those implementations, additional Bluetooth/wireless devices may be installed that detects the proximity of any apparatus 102 in the group that is approaching the hazardous location. In the event of any one child or a group of children approaching a hazardous location, a notification with names may be presented on the client device 104, for example "Ann, Bob, Philip near tank".

Returning to FIG. 9, the interface 900 may include a geo-fence setting button enabling the user of client device 104 to specify one or more geofences for the apparatus(es) 102 associated with the client device 104. For example, the user of client device 104 may be facilitated to create a geo-fence by pressing button 906, to manage the existing geo-fence(s), to edit the existing geo-fence(s), to remove the existing geo-fence(s), and/or any other operations related to the one or more geo-fences after the user presses button 906.

As also shown, the interface 900 may include a general settings button 908 enabling the user of client device 104 to configure the settings of the one or more apparatuses 102 associated with the client device 104. For example, the user of client device 104 may be facilitated to set a threshold upper-limit/lower-limit ambient temperature value, a threshold upper-limit/lower-limit body temperature value, a threshold number of times submersion signals received during a time period to trigger the determination of a drowning situation described above, the length of the time period when the over-temperature condition is detected for generating an over-temperature alert, and/or any other settings of the apparatus 102.

Implementations of the invention may be made in hardware, firmware, software, or various combinations thereof. The invention may also be implemented as instructions stored on a machine-readable medium, which may be read and executed using one or more processing devices. In one implementation, machine-readable media may include various mechanisms for storing and/or transmitting information in a form that can be read by a machine (e.g., a computing device). For example, machine-readable storage media may include read-only memory, random access memory, magnetic disk storage media, optical storage media, flash memory devices, and other media for storing information, and machine-readable transmission media may include forms of propagated signals, including carrier waves, infrared signals, digital signals, and other media for transmitting information. While firmware, software, routines, or instructions may be described in the above disclosure in terms of specific exemplary aspects and implementations performing certain actions, it will be apparent that such descriptions are merely for the sake of convenience and that such actions in fact result from computing devices, processing devices, processors, controllers, or other devices or machines executing the firmware, software, routines, or instructions.

Furthermore, aspects and implementations may be described in the above disclosure as including particular features, structures, or characteristics, but it will be apparent that every aspect or implementation may or may not necessarily include the particular features, structures, or characteristics. Further, where particular features, structures, or characteristics have been described in connection with a specific aspect or implementation, it will be understood that such features, structures, or characteristics may be included with other aspects or implementations, whether or not explicitly described. Thus, various changes and modifications may be made to the preceding disclosure without departing from the scope or spirit of the invention, and the specification and drawings should therefore be regarded as exemplary only, with the scope of the invention determined solely by the appended claims.

What is claimed is:

1. An article of manufacture, comprising a non-transitory processor-readable medium having instructions therein that, when read by a processor, configure the processor to:
- receive an acceleration signal from an accelerometer coupled to the processor;
- receive a submersion signal from a water sensor coupled to the processor;
- detect a first drowning situation when the acceleration signal matches a drowning acceleration signature and the submersion signal and the acceleration signal are generated in a first time period; and
- generate a drowning alert in response to the detection of the first drowning situation.

2. The article of manufacture of claim 1, wherein the processor is further configured to detect at least one of an abduction acceleration signature and a neutral acceleration signature based on the acceleration signal.

3. The article of manufacture of claim 1, wherein the processor is further configured to:
- receive location boundary information for boundaries of one or more areas;
- receive location data from a geolocation device coupled to the processor; and
- determine if the processor is outside a boundary of the one or more areas.

4. The article of manufacture of claim 3, wherein the processor is further configured to generate a wandering alert when the processor detects that it is outside the boundary of the one or more areas and the neutral acceleration signature is detected in a second time period.

5. The article of manufacture of claim 3, wherein the processor is further configured to generate an abduction alert when the processor detects that it is outside the boundary of the one or more areas and the abduction acceleration signature is detected in a second time period.

6. An apparatus, comprising:
- a processor;
- a body temperature sensor coupled to the processor, configured to measure a body temperature of a user of the apparatus and to generate a body temperature signal;
- a heart rate sensor coupled to the processor, configured to measure a heart rate of the user,
- wherein the processor is configured to generate a hyperthermia alert when the body temperature of the user exceeds a predetermined upper-limit body temperature threshold and when the heart rate of the user exceeds a predetermined upper-limit heart rate threshold, and
- wherein the processor is configured to generate a hypothermia alert when the body temperature of the user drops below a predetermined lower-limit body temperature threshold and when the heart rate of the user drops below a predetermined lower-limit heart rate threshold.

7. A method for tracking personal safety via an apparatus worn by a user, the apparatus comprising a processor, a memory coupled to the processor containing instructions to configure the processor, a body temperature sensor coupled to the processor and a heart rate sensor coupled to the processor, the method comprising:
- measuring a body temperature of the user and generating a body temperature signal;
- measuring a heart rate of the user and generating a heart rate signal;
- generating a hyperthermia alert when the body temperature of the user exceeds a predetermined upper-limit body temperature threshold and when the heart rate of the user exceeds a predetermined upper-limit heart rate threshold; and
- generating a hypothermia alert when the body temperature of the user drops below a predetermined lower-limit body temperature threshold and when the heart rate of the user drops below a predetermined lower-limit heart rate threshold.

8. An article of manufacture, comprising a non-transitory processor-readable medium having instructions therein that, when read by a processor, configure the processor to:
- detect a body temperature signal from a body temperature sensor coupled to the processor;
- detect a heart rate signal from a heart rate sensor coupled to the processor;
- generate a hyperthermia alert when the detected body temperature exceeds a predetermined upper-limit body temperature threshold and when the detected heart rate exceeds a predetermined upper-limit heart rate threshold; and
- generate a hypothermia alert when the detected body temperature drops below a predetermined lower-limit body temperature threshold and when the detected heart rate drops below a predetermined lower-limit heart rate threshold.

* * * * *